US012753429B2

(12) United States Patent
Deshpande et al.

(10) Patent No.: US 12,753,429 B2
(45) Date of Patent: Oct. 6, 2026

(54) METHODS AND SYSTEMS FOR AUTOMATED COUNTING AND CLASSIFYING COLONIES OF MICROORGANISMS

(71) Applicant: AIRAMATRIX PRIVATE LIMITED, Thane (IN)

(72) Inventors: Ameya Dilip Deshpande, Thane-West (IN); Dinisha Suresh Kadam, Navi Mumbai (IN); Geetank Raipuria, Mumbai (IN)

(73) Assignee: AIRAMATRIX PRIVATE LIMITED, Thane (IN)

( * ) Notice: Subject to any disclaimer, the term of this patent is extended or adjusted under 35 U.S.C. 154(b) by 715 days.

(21) Appl. No.: 17/147,135

(22) Filed: Jan. 12, 2021

(65) Prior Publication Data

US 2021/0214765 A1 Jul. 15, 2021

(30) Foreign Application Priority Data

Jan. 13, 2020 (IN) ............................ 202021001509

(51) Int. Cl.

| | |
|---|---|
| ***C12Q 1/06*** | (2006.01) |
| ***C12M 1/34*** | (2006.01) |
| ***G06T 7/00*** | (2017.01) |
| ***G06V 10/82*** | (2022.01) |
| ***G06V 20/69*** | (2022.01) |

(52) U.S. Cl.

CPC ............... *C12Q 1/06* (2013.01); *C12M 41/36* (2013.01); *G06V 10/82* (2022.01); *G06T 7/0002* (2013.01); *G06T 2207/20084* (2013.01); *G06T 2207/30168* (2013.01); *G06V 20/695* (2022.01)

(58) Field of Classification Search

None

See application file for complete search history.

(56) References Cited

PUBLICATIONS

Choudhry, Priya. "High-throughput method for automated colony and cell counting by digital image analysis based on edge detection." PloS one 11.2 (2016): e0148469.*

Xie, Weidi, J. Alison Noble, and Andrew Zisserman. "Microscopy cell counting and detection with fully convolutional regression networks." Computer methods in biomechanics and biomedical engineering: Imaging & Visualization 6.3 (2018): 283-292.*

* cited by examiner

*Primary Examiner* — G. Steven Vanni

(74) *Attorney, Agent, or Firm* — Maschoff Brennan

(57) ABSTRACT

Methods and systems for automated counting and classifying microorganisms. A method disclosed herein includes receiving and analyzing quality of at least one input media of at least one incubated dish used for growth of the colonies of the microorganisms. The method further includes detecting the colonies of the microorganisms in a growth medium disposed on the dish if the received at least one media is a good quality media, wherein the detected colonies include at least one of individual colonies and grouped colonies. The method further includes segregating the grouped colonies into the individual colonies. The method further includes classifying the individual colonies into at least one species of the microorganisms. The method further includes counting the colonies of each species.

12 Claims, 10 Drawing Sheets

METHODS AND SYSTEMS FOR AUTOMATED COUNTING AND CLASSIFYING COLONIES OF MICROORGANISMS

TECHNICAL FIELD

Embodiments disclosed herein relate to management of microorganisms in a growth medium, and more particularly to an automated counting and classifying of microorganisms in a growth medium.

BACKGROUND

Typically, colonies of microorganisms (such as, but not limited to, bacteria, fungus, or the like) grow in a medium (such as an agar medium) disposed in a dish. The dish may be mounted on a reading apparatus having a light source arranged therein, wherein light is directed through the medium to increase visibility of the colonies of the microorganisms in the medium. Examples scenarios where the microorganisms need to be counted are monitoring a clean room environment, vitro biological evaluation (an Ames test or the like), and so on.

In conventional approaches, trained technicians/operators may count the colonies of the microorganisms manually based on the light directed through the medium disposed in the dish. However, such a process of counting the colonies of the microorganisms manually may be subjected to errors, particularly where the number of dishes and the number of colonies are large. Also, the number of colonies counted by the technician may be a running total, which may not always be true. Further, the technician may not always be having sufficient knowledge to handle confluent growth or growth of colonies that touch or overlap other colonies, identify each colony as a unit in spite of differing shapes, sizes, textures, colors, light intensities, and so on, classify between bacterial and fungal colonies, or the like.

Further, in the conventional approaches, laboratories may use a huge volume of dishes to accommodate extremely large counts of the colonies. In such a scenario, the counting of the colonies by the technician can be a significant budgetary and technical hurdle for the laboratories.

SUMMARY

The principal object of embodiments herein is to disclose methods and systems for automatically counting colonies of microorganisms in a growth medium.

Another object of embodiments herein is to disclose methods and systems for detecting the colonies of the microorganisms in the growth medium, wherein the colonies of the microorganisms include at least one of individual colonies of the microorganisms, and merged/overlapped colonies of the microorganisms.

Another object of embodiments herein is to disclose methods and systems for segregating the merged/overlapped colonies of the microorganisms.

Another object of embodiments herein is to disclose methods and systems for classifying the individual colonies of the microorganisms into at least one species/type of the microorganisms.

Another object of embodiments herein is to disclose methods and systems for counting the colonies of each species/type of the microorganisms.

These and other aspects of the embodiments herein will be better appreciated and understood when considered in conjunction with the following description and the accompanying drawings. It should be understood, however, that the following descriptions, while indicating at least one embodiment and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

Embodiments herein are illustrated in the accompanying drawings, throughout which like reference letters indicate corresponding parts in the various figures. The embodiments herein will be better understood from the following description with reference to the drawings, in which.

DETAILED DESCRIPTION

Figure 1A:
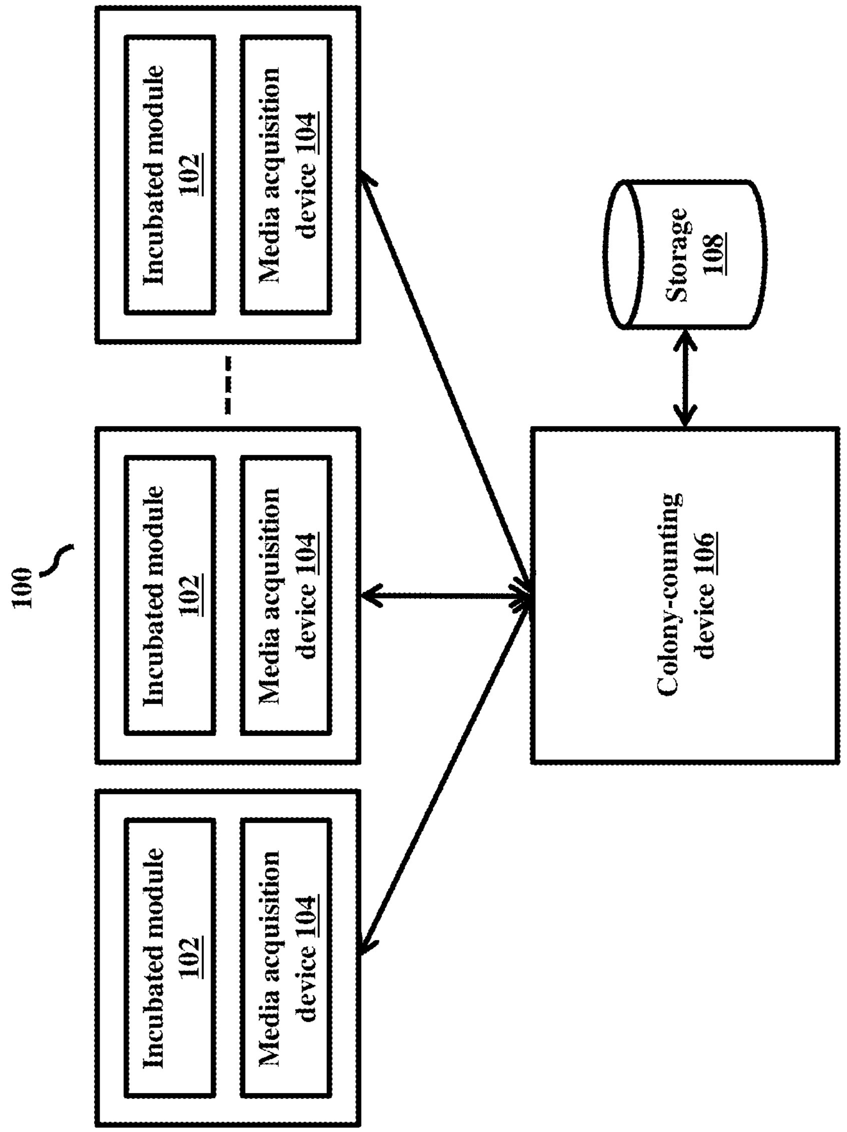
FIGS. 1*a* and 1*b* depict a colony counting system, according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Embodiments herein disclose methods and systems for automatically counting colonies of microorganisms in a growth medium by detecting the colonies in the growth medium and classifying the detected colonies into at least one type of microorganisms. Referring now to the drawings, and more particularly to FIGS. 1*a* through 9, where similar reference characters denote corresponding features consistently throughout the figures, there are shown embodiments.

Figure 1B:
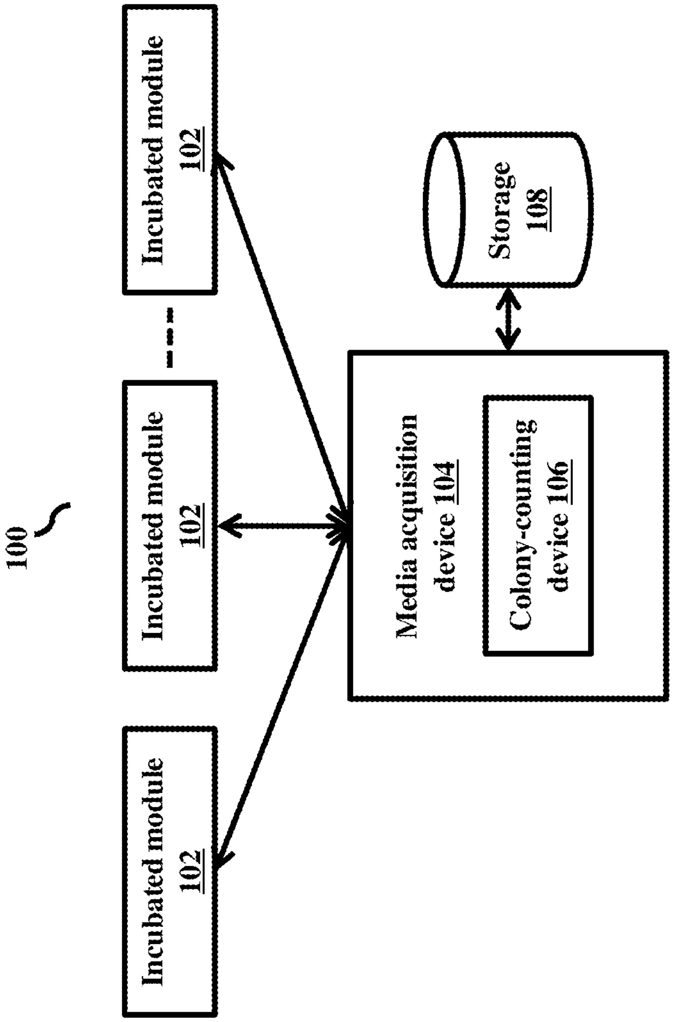

FIGS. 1*a* and 1*b* depict a colony counting system 100, according to embodiments as disclosed herein. The colony counting system 100 can be configured to digitize/automate a process of counting of colonies of microorganisms. Examples of the microorganisms can be, but not limited to, bacteria, fungus, small mosses, and so on. In an embodiment herein, the colonies of the microorganisms can include a cluster of identical cells derived from a single parent cell of the microorganisms. The process of counting of the colonies of the microorganisms can be used in applications such as, but not limited to, clean room environment monitoring/microbial evaluation (drug formulation or the like), vitro biological evaluation/tests (an Ames test or the like), and so on.

As depicted in FIG. 1*a*, the colony counting system 100 includes a plurality of incubation modules 102, a plurality of media acquisition devices 104, a colony-counting device 106, and a storage 108.

The incubation module(s) 102 can be a colony culturing apparatus including a dish. The incubation module 102 can be configured to incubate the dish for growing/culturing the microorganisms in a growth medium disposed on the dish. The dish can be a plated media used for growth or culture of cells of the microorganisms. Examples of the dish can be, but is not limited to, a Petri dish, a slide, or the like. The growth medium can be a culture medium including nutrients and physical growth parameters required for the growth of the microorganisms on the dish. Examples of the growth medium can be, but not limited to, a solid medium, a semisolid medium, a liquid medium, and so on. The medium can include at least one of agar, gelatin or the like. The medium includes nutrients for the growth of the microorganisms.

The media acquisition device(s) 104 referred herein can be at least one of a camera, a scanner, an imaging sensor, a digital camera, a thermal camera, an ultraviolet (UV) camera, a multispectral camera, a microscope, an electron microscope, and so on. The media acquisition device(s) 104 can be communicatively coupled with the at least one incubation module 102 including the dish. The media acquisition device 104 can also be connected to the colony-counting device 106 using a communication network. Examples of the communication network can be, but not limited to, the Internet, a wired network, a wireless network (a Wi-Fi network, a cellular network, a Wi-Fi Hotspot, Bluetooth, Zigbee and so on) and so on.

The media acquisition device 104 can be configured to acquire at least one media of the incubated dish of the at least one incubation module 102, wherein the incubated dish may be or may not be including the at least one colony of the at least one microorganism. Also, a user/operator/technician of the incubation module 102 may acquire the at least one media of the incubated dish using the at least one media acquisition device 104. The at least one media acquired by the media acquisition device 104 can be an optical image, video, and so on. The media acquisition device 104 can be further configured to communicate the acquired at least one media of the incubated dish to the colony-counting device 106 using the communication network.

The colony-counting device 106 can be at least one of a cloud computing device (can be a part of a public cloud or a private cloud), a server, a computing device, and so on. The server may be at least one of a standalone server, a server on a cloud, or the like. The computing device can be, but not limited to, a personal computer, a notebook, a tablet, desktop computer, a laptop, a handheld device, a mobile device, and so on. Also, the colony counting device 106 can be at least one of a microcontroller, a processor, a System on Chip (SoC), an integrated chip (IC), a microprocessor based programmable consumer electronic device, and so on. The colony-counting device 106 can connect to the plurality of media acquisition devices 104, the storage 108 and user devices (used by the user/technician) using the communication network. In an embodiment, the colony-computing device 106 can be remotely located from the plurality of media acquisition devices 104. In an embodiment, the at least one media acquisition device 104 can be the colony-counting device 106 and can perform intended functions of the colony-counting device 106, as depicted in FIG. 1*b*.

The colony-counting device 106 can be configured to count the colonies of the microorganisms grown in the growth medium disposed on the dish. In an embodiment, the colony-counting device 106 counts the colonies of the microorganisms by detecting the colonies in the growth medium and classifying the detected colonies into at least one species/type of microorganisms.

The colony-counting device 106 receives the acquired at least one media of the incubated dish from the at least one media acquisition device 104. The colony-counting device 106 analyzes the quality of the received media of the incubated dish and classifies the received media into at least one quality type. Examples of the at least one quality type can be, but not limited to, good quality media, and low quality media.

In an embodiment, the colony-counting device 106 may use reference based methods to analyze the quality of the received media of the incubated dish. The reference based methods involve using at least one reference media for classifying the received media into the at least one quality type. The reference media can be at least one of an image, a video, and so on captured using optimal optical settings without any disturbance. The reference media may be the media without including any colonies of the microorganisms. The colony-counting device 106 may access the storage 108 for the reference media. The colony-counting device 106 may also communicate with at least one external device (for example: an external server, an external database, and so on) for receiving the reference media. The colony-counting device 106 compares the received media of the incubated Petri dish with the reference media and generates a structural similarity index measurement (SSIM). The SSIM can indicate measurement of similarities between the received media and the reference media. The colony-counting device 106 compares the generated SSIM with a pre-defined SSIM threshold. If the generated SSIM satisfies the SSIM threshold (for example, the generated SSIM is greater than or equal to the pre-defined SSIM threshold), the colony-counting device 106 classifies the received media into the good quality media. If the generated SSIM does not satisfy the pre-defined threshold (for example, the generated SSIM is less than the pre-defined SSIM threshold), the colony-counting device 106 classifies the received media into the low quality media.

In an embodiment, the colony-counting device 106 may use non-reference methods to analyze the quality of the received media of the incubated dish. The non-reference methods may involve unsupervised learning methods/techniques to classify the received media into the at least one quality type. The colony-counting device 106 encodes data of the received media (such as, but not limited to, resolution, frame rate, texture, morphology, colour, and so on) and compresses the encoded data to provide an encoded representation for the received media. The colony-counting device 106 further generates an output media by reconstructing data back from the encoded representation. The colony-counting device 106 identifies difference(s) between the received media and the generated the output media (for example, difference in resolution, frame rate, pixel intensity, blur, and so on). If the identified difference(s) does not satisfy a pre-defined difference threshold (for example: the identified difference is greater than or equal to the pre-defined threshold), the colony-counting device 106 classifies the received media into the low quality media. If the identified difference(s) satisfies the pre-defined difference threshold (for example: the identified difference is less than the pre-defined difference threshold), the colony-counting device 106 classifies the received at least one media into the good quality media. After analyzing the quality of the received media, the colony-counting device 106 checks if the received media is good quality media. If the received media is not a good quality media (i.e., the received media is a low quality media), the colony-counting device 106 provides commands to the corresponding at least one media acquisition device 104 to re-acquire the media. If the received media is the good quality media, the colony-counting device 106 classifies/segregates the received media into a media with detected colonies of the microorganisms that might be grown in the growth medium disposed on the dish and a media with no colonies of the microorganisms (zero colonies).

In an embodiment, for detecting the colonies of the microorganisms, the colony-counting device 106 separates foreground regions from background regions of the received media. The foreground regions may indicate the colonies of the microorganisms and background regions may indicate the dish with the growth medium. The colony-counting device 106 detects the features of the foreground regions by performing a downscaling and an up scaling of the foreground regions. Examples of the features can be, but not limited to, color, texture, edges, corners, and so on. The colony-counting device 106 maps the detected features with labelled training data to detect the media with the colonies of the microorganisms. The labelled training data includes a plurality of original media including the specific colony of the microorganisms and associated label feature data. The label feature data can indicate original image features such as, but not limited to, color, texture, edges, corners, and so on. If the detected features map with one of the label feature data of the at least one original media (included in the labelled training data), then the colony-counting device 106 detects that the colonies of the microorganisms corresponding to the mapped labelled training data are present in the growth media and classifies the received media into the media with the detected colonies of the microorganisms. The detected colonies can be individual colonies of the microorganisms and/or a cluster of colonies of the microorganisms (grouped/merged/overlapped colonies), or the like. If the detected features do not map with any one of the label feature data (included in the labelled training data), the colony-counting device 106 classifies the received media into the media with the zero colonies of the microorganisms.

If the detected colonies are merged/overlapped colonies, the colony-counting device 106 separates/segregates the merged colonies/overlapped colonies of the microorganisms into individual colonies of the microorganisms.

In an embodiment, the colony-counting device 106 segregates the merged colonies using a distance transform of the media including the detected colonies and image processing methods. The distance transform can be a gray scale/level media generated by changing gray level intensities of points inside the foreground regions of the media including the detected colonies and illustrating a distance to a closest boundary from each point. For computing the distance transform, the colony-counting device 106 converts the media including the detected colonies into binary media. In an embodiment, the colony-counting device 106 generates the gray level media from the binary media by changing the gray level intensities of the points present inside the foreground regions/detected colonies of the media and illustrating the distance from each pixel (each point in the foreground regions/detected colonies) to a non-zero valued pixel (that indicates the closest boundary). In an embodiment, the colony-counting device 106 generates the gray level media from the binary media based on a Euclidean distance measure. The colony-counting device 106 then applies the image processing methods such as, but not limited to, a watershed segmentation method, or the like on the gray level media/distance transform to segregate the merged colonies into the individual colonies of the microorganisms.

After segregating the merged colonies into the individual colonies, the colony-computing device 106 classifies/quantifies the individual colonies of the microorganisms into at least one species/type/class of the microorganisms. The at least one species can be at least one of bacteria, fungus, or other/unknown microorganism. In an embodiment herein, a deep learning based mask residual-convolution neural network (RCNN) model may be used for classifying the colonies.

For classifying the individual colonies into the at least one species of microorganisms, the colony-counting device 106 performs scanning of a feature map level of the media including the individual colonies and generates proposals about regions in the media that includes the objects/individual colonies. Examples of the feature maps can be, but not limited to, Histograms of Oriented Gradients (HOG), Local Binary Pattern (LBP), and so on. The colony-counting device 106 generates a feature pyramid map using the media including the colonies of specific species of the microorganisms, assigns the proposed regions to specific areas of the feature pyramid map and scans the assigned areas. The colony-counting device 106 further maps the scanned areas with a multi-categorical classification to classify the detected individual colonies into the at least one species/type/class of microorganisms, wherein the multi-categorical classification includes information about the feature map levels/areas of the plurality of colonies and the associated type/species. The colony-counting device 106 also generates bounding boxes or free form contours for the detected individual colonies/objects, and a mask in a pixel level of the object/colonies by refining the generated bounding boxes or the free form contours. The bounding boxes and the free form contours may indicate boundaries of the detected colonies. The free form contours may be in a shape of at least one of a square, a rectangle, a circle, an oval, and so on. The mask can be output pixel overlays indicating the bounding boxes of the objects/colonies and a label for the generated bounding box of each colony, wherein the label includes information about the detected class/type/species of microorganisms.

The colony-computing device 106 may further reclassify the other/unknown microorganisms into the at least one class/species. In an embodiment, the colony-computing device 106 provides the output pixel overlays/mask indicating the classification of the individual colonies into the at least one species of the microorganisms to the user/technician to confirm that no colonies in the dish is missed from the classification. Thus, improving accuracy and precision of the colony counting. The colony-computing device 106 further receives inputs from the technician related to the classification of the individual colonies of the microorganisms. The inputs can indicate that the individual colonies of the microorganisms are classified into the correct species or incorrect species. The inputs can also indicate the correct species for the individual colonies of the microorganisms/unknown microorganisms. Based on the inputs from the user/technician, the colony-computing device 106 re-classifies the individual colonies of the microorganisms/unknown microorganisms into the at least one species. In order to re-classify the individual colonies of the microorganisms/unknown microorganisms, the colony-counting device 106 corrects the label associated with the colony(ies) based on the inputs received from the user. The colony-counting device 106 further uses the corrected label as the multi-categorical classification and re-classifies the individual colonies/unknown microorganisms into the at least one class/species of microorganisms.

The colony-counting device 106 counts the colonies of each species of the microorganisms based on the classification/re-classification of the individual colonies of the microorganisms. In an embodiment herein, the colony-counting device 106 can count the colonies by adding a number of each type/species of the classified colonies. The colony-computing device 106 generates a statistics report indicating the count of the colonies of the microorganisms. Thus, the automated/digitized counting of the colonies of the microorganisms can be less error prone and fast, which further increases the throughput of the system 100.

The storage 108 can store at least one of information about the media acquisition devices 104, the reference media, the received media of the incubated dish and the output media/pixel overlays generated for the received media (indicating the classification of the individual colonies of the microorganisms into the at least one species), information about the counted colonies of each species, and so on. The storage 108 can be at least one of a database, a file server, a data server, a server, cloud storage and so on.

FIGS. 1*a* and 1*b* show exemplary blocks of the colony counting system 100, but it is to be understood that other embodiments are not limited thereon. In other embodiments, the colony counting system 100 may include less or more number of blocks. Further, the labels or names of the blocks are used only for illustrative purpose and does not limit the scope of the embodiments herein. One or more blocks can be combined together to perform same or substantially similar function in the colony counting system 100.

Figure 2:
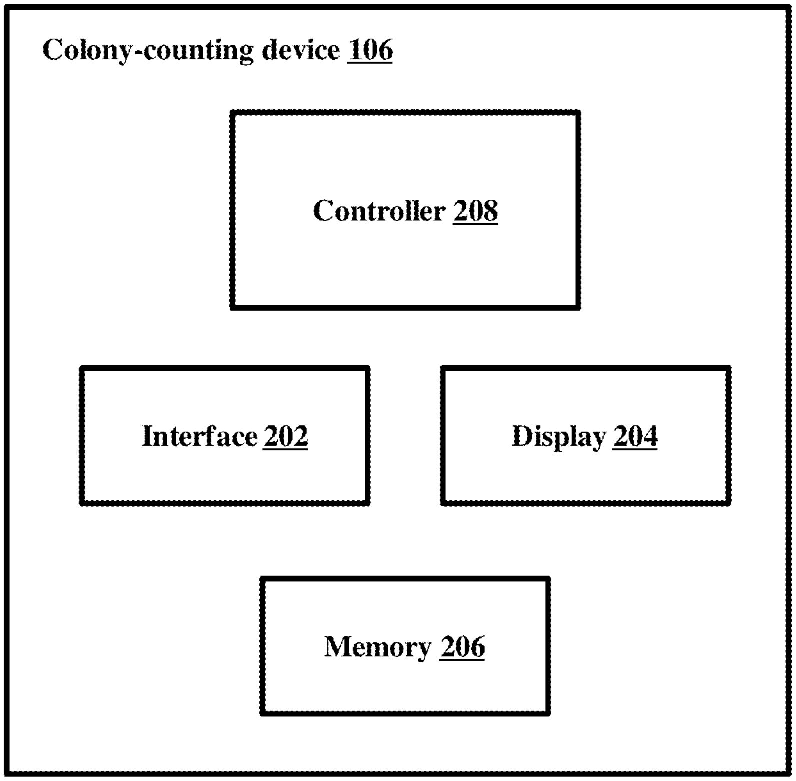
FIG. 2 is a block diagram illustrating various components of a colony-counting device, according to embodiments as disclosed herein.

FIG. 2 is a block diagram illustrating various components of the colony-counting device 106, according to embodiments as disclosed herein. The colony-counting device 106 includes an interface 202, a display 204, a memory 206, and a controller 208.

The interface 202 can be configured to enable the colony-counting device 106 to communicate with at least one external entity using the communication network. The at least one external entity can be, but not limited to, the plurality of media acquisition devices 104, the storage 108, the user devices used by the users/technicians, and so on. The interface 202 can also include physical ports that can be configured to enable the colony-counting device 106 to communicate with additional devices/modules. Examples of the physical ports can be, but not limited to, general-purpose input/output (GPIO), Universal Serial Bus (USB), Ethernet, Camera Serial Interface (CSI), Display Serial Interface (DSI), and so on. Examples of the additional devices/modules can be, but not limited to, On-board diagnostics (OBD) ports, the media acquisition devices 104, cameras, sensors, and so on.

The display 204 can be configured to enable the user/technician to interact with the colony-counting device 106. The display 204 can be used to provide information to the users in a form of text, visual alerts, and so on. The information can be at least one of the information about the received media of the incubated dish (the input media), the output pixels overlays indicating the classification of the individual colonies of the microorganisms into the at least one species, and so on.

The memory 206 can store at least one of the received media of the incubated dish (the input media), the at least one reference image/base media for the quality analysis of the received media, information about the detected individual/merged/overlapped colonies, the output pixels overlays (indicating the classification of the individual colonies of the microorganisms into the at least one species), and so on. The memory 206 also includes code that can be executed on the controller 208 to perform one or more steps for counting of the colonies of the microorganisms. Examples of the memory 206 can be, but not limited to, NAND, embedded Multi Media Card (eMMC), Secure Digital (SD) cards, Universal Serial Bus (USB), Serial Advanced Technology Attachment (SATA), solid-state drive (SSD), and so on. The memory 206 may also include one or more computer-readable storage media. The memory 206 may also include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. In addition, the memory 206 may, in some examples, be considered a non-transitory storage medium. The term "non-transitory" may indicate that the storage medium is not embodied in a carrier wave or a propagated signal. However, the term "non-transitory" should not be interpreted to mean that the memory 206 is non-movable. In certain examples, a non-transitory storage medium may store data that can, over time, change (e.g., in Random Access Memory (RAM) or cache).

The controller 208 can be at least one of a single processer, a plurality of processors, multiple homogeneous or heterogeneous cores, multiple Central Processing Units (CPUs) of different kinds, microcontrollers, special media, and other accelerators. The controller 208 can be configured to count the colonies of the microorganisms in the growth medium disposed on the dish.

Figure 3:
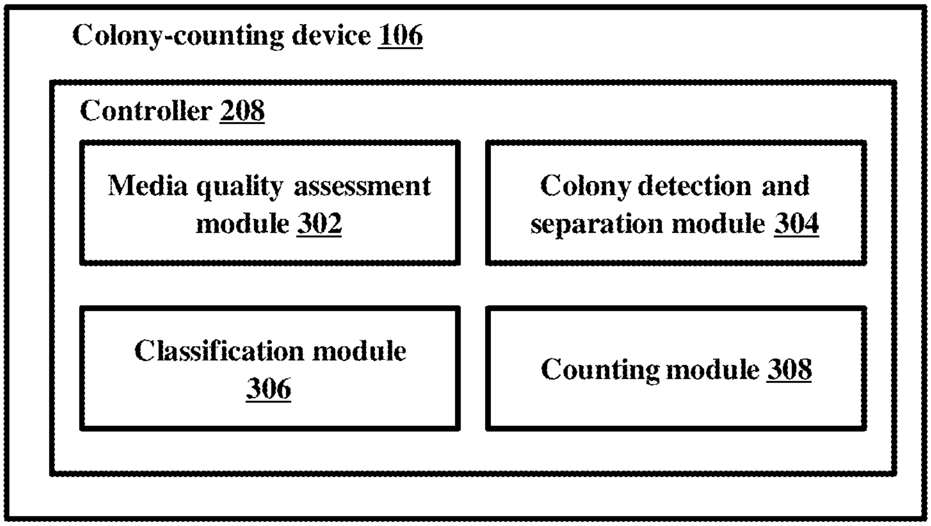
FIG. 3 is a block diagram illustrating various components of a controller of the colony-counting device for counting colonies of microorganisms in a growth medium, according to embodiments as disclosed herein.

As depicted in FIG. 3, the controller 208 includes a media quality assessment module 302, a colony detection and separation module 304, a classification module 306, and a counting module 308 for counting the colonies of the microorganisms in the growth medium.

The media quality assessment module 302 can be configured to receive the at least one input media from the at least one media acquisition device 104 and analyze the quality of the received input media. The input media can be the at least one media (the optical image, the video, or the like) of the incubated dish with the growth medium, wherein the dish may or may not include the colonies of the microorganisms.

In an embodiment, the media quality assessment module 302 may use the reference based methods for analyzing the quality of the input media. The media quality assessment module 302 maintains the at least one reference media/base media in the memory 206/storage 108 for analyzing the quality of the input media. The reference media can be at least one of a high/good quality image, a high/good quality video, or the like and captured using the optimal optical settings without any disturbance. The reference media can be the media without including any colonies of the microorganisms. The media quality assessment module 304 extracts the background regions of the input media that include the dish. The media quality assessment module 304 compares the extracted background regions of the input media with the reference media and computes the SSIM. In an example, the SSIM can be computed as:

$$SSIM(a, b) = \frac{(2\mu_a\mu_b + c_1)(2\sigma_{ab} + c_2)}{(\mu_a^2 + \mu_b^2 + c_1)(\sigma_a^2 + \sigma_b^2 + c_2)}$$

wherein, 'a' represents the reference media, 'b' represents the input media, '$\mu_a$' represents a mean value of the reference media, '$\mu_b$' represents a mean value of the background regions of the input media, '$\sigma_a^2$' represents a variance of the reference media,

'$\sigma_b^2$' represents a variance of the background regions of the input media, '$\sigma_{ab}$' represents a co-variance between the reference media and the background regions of the input media, '$c_1$' and '$c_2$' represent scalar constants to stabilize a division denominator.

The media quality assessment module 302 uses the computed SSIM to classify the input media into the at least one quality type. The at least one quality type can be at least one of the good quality media, and the low quality media. The media quality assessment module 302 compares the computed SSIM with the pre-defined SSIM threshold. The pre-defined SSIM threshold can be set based on an ideal SSIM value computed using the high quality reference media. The media quality assessment module 302 classifies the input media into the good quality media, if the computed SSIM is greater than or equal to the pre-defined SSIM threshold. The media quality assessment module 302 classifies the input media into the low quality media, if the computed SSIM is lesser than the pre-defined SSIM threshold.

In an embodiment, the media quality assessment module 302 may use the non-reference-based methods to analyse the quality of the input media. The non-reference based methods do not require any reference media for analyzing the quality of the input media and involve the unsupervised learning techniques for analyzing the quality of the input media. The media quality assessment module 302 includes an auto-encoder and a decoder for analyzing the quality of the input media in accordance with the non-reference based methods. The media quality assessment module 302 feeds the received input media of the dish to the auto-encoder, wherein the auto-encoder can be trained initially with the good quality media. The auto-encoder extracts the data such as, but not limited to, resolution, frame rate, texture, morphology, color, pixel intensity, and so on associated with the input media and constructs the encoded data representation by encoding the extracted data. The auto-encoder passes the encoded data representation to the decoder, which re-constructs the output media for the received input media using the encoded data representation. The image assessment module 302 detects the differences between the output media and the input media and accordingly classifies the received input media into at least one of the good quality media, and the low quality media. In an example herein, the differences can be at least one of change in the resolution of the output image, change in the frame rate of the output image, change in the pixel intensity, change in the texture, change in the color, and so on. The image assessment module 302 compares the detected differences with the pre-defined difference threshold for classifying the input media into the at least one quality type. The pre-defined difference threshold can indicate difference values observed for the high quality reference media. If the detected differences are greater than/equal to the pre-defined difference threshold, the image assessment module 302 classifies the input media into the low quality media. If the detected differences are lesser than the pre-defined difference threshold, the image assessment module 302 classifies the input media into the good quality media.

After classifying the input media into the at least one quality type, the media quality assessment module 302 checks the quality type of the input media. If the input media is classified into the low quality media, the media quality assessment module 302 provides the commands to the corresponding at least one media acquisition device 104 to re-acquire the at least one media of the dish. If the input media is classified into the good quality media, the media quality assessment module 302 provides the input media to the colony detection and separation module 304 for detecting the colonies of the microorganisms in the growth medium disposed on the dish.

The colony detection and separation module 304 can be configured to detect the colonies of the microorganisms in the growth medium disposed on the dish by evaluating the input media received from the media quality assessment module 302. In an embodiment, the colony detection and separation module 304 may use neural network processing methods, such as, but not limited to, a machine learning (ML), a convolutional neural network (CNN), an artificial intelligence (AI), and so on for detecting the colonies of the microorganisms in the growth medium. Embodiments herein are further explained considering the CNN with a residual network (ResNet) as an example for detecting the colonies of the microorganisms in the growth medium, but it may be obvious to a person skilled in the art that any other processing methods may be used. The CNN with the ResNet may include at least one encoding path and at least one decoding path, wherein the encoding path may be paired with a decoding path. The encoding path may include an initial processing block and a plurality of processing stages/layers. The initial processing block includes convolution+Batchnorm+RectifiedLinearActivation (ReLu) (CBN) layer and a max pooling layer. Each processing stage includes a convolution block and an identity block. The convolution block and the identity block may include a plurality of convolutional layers. The decoding path may include a spatial pyramid pool (SPP), convolution layer (C), an element wise summer (EWS) block, and a deconvolution layer (DC).

The colony detection and separation module 304 feeds the received input media from the image assessment module 302 to the encoding path of the CNN with the ResNet. The initial processing block of the encoding path may separate the foreground regions from the background regions of the input media, and provides the foreground regions of the media to the plurality of processing stages of the encoding path. Each processing stage may downscale the media and extract the features of the foreground regions such as, but not limited to, color, texture, edges, corners, and so on and provide the extracted features to the next processing stages using a skip connection. The extracted features at each processing stage may be provided to the decoding path, which detects the colonies in the encoding path based on the labelled training data. The labelled training data includes the plurality of original media including the specific colony of the microorganisms and the associated label feature data. The label feature data can indicate original image features such as, but not limited to, color, texture, edges, corners, and so on. The colonies can be detected if the associated extracted features successful maps with the label feature data of the corresponding colonies (included in the labelled training data). The detected colonies can be the individual colonies of the microorganisms, the merged/grouped colonies of the microorganisms, the overlapped colonies of the microorganisms, and so on. On detecting the colonies, the colony detection and separation module 304 segregates the input media into the media with the colonies of the microorganisms. If the extracted features do not match with the label feature data, then the decoding path may determine that there may be absence of growth of the colonies in the growth medium disposed on the dish (zero colonies in the growth medium disposed on the dish). In such a case, the colony detection and separation module 304 segregates the input media into the media with the zero colonies of the microorganisms. On segregating the media with the zero colonies, the colony detection and separation module 304 communicates to the user/user device that there are no colonies present in the growth medium disposed on the dish.

The colony detection and separation module 304 checks if the detected colonies are the merged/overlapped colonies, or the individual colonies, on segregating the input media into the media with the colonies of the microorganisms. If the detected colonies are the individual colonies, the colony detection and separation module 304 provides the media with the detected colonies to the classification module 306. If the detected colonies are the merged colonies/overlapped colonies, the colony detection and separation module 304 separates the merged/overlapped colonies into the individual colonies of the microorganisms and provides the separated individual colonies to the classification module 306.

For separating the merged/overlapped colonies, the colony detection and separation module computes the distance transform, a gray level/scale media for the media including the merged colonies. For computing the distance transform, the colony detection and separation module 304 identifies the foreground regions of the media that include the detected colonies (the merged colonies) and converts the foreground regions into the binary media. In an embodiment herein, the colony detection and separation module 304 can generate the gray level media from the binary media based on the Euclidean distance measure. In an embodiment herein, the colony detection and separation module 304 can generate the gray level media from the binary media by changing the gray scale/level intensities of the points present inside the foreground regions/detected colonies of the media and illustrating the distance from each pixel (each point in the foreground regions/detected colonies) to the non-zero valued pixel (that indicates the closest boundary). The gray level media with the changed gray level intensities and including the illustration of the distance from each pixel (each point in the foreground regions/detected colonies) to the non-zero valued pixel (that indicates the closest boundary) may represent the distance transform. The colony detection and separation module 304 applies the image processing methods, such as, but is not limited to, a watershed segmentation method, or the like on the distance transform to separate the merged colonies into the individual colonies of the microorganisms.

Embodiments herein are further explained considering the watershed segmentation method as an example for separating the merged colonies, but it may be obvious to a person skilled in the art that any other image processing methods may be considered.

For separating the merged colonies using the watershed segmentation method, the colony detection and separation module 304 visualizes the gray level/scale media/distance transform as a topographic surface with the gray level intensities, wherein the gray level intensities include at least one of the points of the high intensity that denotes peaks and hills, and points of the low intensity that denotes valleys. The colony detection and separation module 304 fills every isolated valley (local minima) with different colored water/labels. As the water raises/labels raises, the different valleys with the different colored water may merge depending on the peaks nearby. In order to avoid the merging, the colony detection and separation module 304 further builds barriers in locations, where the different valleys with the different colored water/labels merge. The colony detection and separation module 304 recursively fills the isolated valleys with the different colored water and builds the barriers in the locations where the different valleys with the different colored water/labels merge until all the peaks are underwater. The barriers built may represent the segregation/separation of the merged colonies.

The classification module 306 can be configured to classify the individual colonies of the microorganisms into the at least one species/types. The at least one species can be, but not limited to, the bacteria, the fungus, or any other unknown microorganism.

In an embodiment, the colony detection and separation module 304 may use neural network processing methods, such as, but not limited to, a machine learning (ML), a convolutional neural network (CNN), an artificial intelligence (AI), and so on for classifying the colonies of the microorganisms in the growth medium. Embodiments herein are further explained considering a mask residual-CNN (RCNN) as an example for classifying the microorganisms into the at least one type, but it may be obvious to a person skilled in the art that any other processing methods may be used. In an example, the mask RCNN referred herein can be a feature pyramid network (FPN) based deep neural network including a backbone structure. The mask RCNN may consist of a bottom-up pathway (for example: a ConvNet, a ResNet, and so on), a top-bottom pathway, and lateral connections, wherein the bottom-up pathway and the top-bottom pathway may be connected to the backbone structure/lateral connections. The lateral connections may include convolution and adding operations between the two corresponding levels of the bottom-up pathway and the top-bottom pathway. The bottom-up pathway, the top-bottom pathway, and the lateral connections may include at least one of a CNN backbone, a Region Proposal Network (RPN), pooling layers, a mask branch, and fully connected layers.

The classification module 306 may feed the media with the individual colonies into the bottom-up pathway of the mask RCNN. The bottom-up pathway scans the feature map level of the received media and proposes/predicts the regions with the objects/colonies. The top-bottom pathway generates the feature pyramid map, which can be similar to the feature map scanned by the bottom-up pathway. The feature pyramid map can be a map including the feature maps derived from the colonies of specific species. The top-bottom pathway assigns the predicted regions to specific areas of the feature pyramid maps, and maps the assigned specific areas of the feature pyramid maps with the multi-categorical classification to classify the detected individual colonies into the at least one species/type/class of microorganisms, wherein the multi-categorical classification includes information about the feature map levels/areas of the plurality of colonies and the associated type/species. The top-bottom pathway selects the species among the species present in the multi-categorical classification as the species for the detected individual colonies, if the associated feature map levels successful match with the specific areas of the feature pyramid maps assigned to the predicted regions with the individual colonies. The top-bottom pathway may also generate the bounding boxes or the free form contours for the objects/colonies present in the predicted regions, wherein the bounding boxes or the free form contours may indicate boundaries of the detected colonies. The free form contours can be of shapes such as, but not limited to, a square, a rectangle, a circle, an oval, and so on. The top-bottom pathway may also generate the mask for the detected colonies by refining the generated bounding boxes or the free form contours. The mask can be output pixel overlays indicating the bounding boxes or the free form contours of the objects/colonies and the label for the generated bounding box of each colony, wherein the label includes information about the detected class/type/species of microorganisms.

The classification module 306 can be further configured to re-classify the classified colonies/other/unknown microorganisms into at least one of the bacteria, the fungus, or the like.

The classification module 306 can be further configured to provide the output pixels overlays of the media indicating the classification of the individual colonies into the at least one species to the user for validating the classification of the individual colonies. The classification module 306 may further receive the inputs from the user related to the classification of the individual colonies. The inputs can indicate that the individual colonies are classified into the correct/incorrect species, the correct species for the individual colonies, the species for the unknown microorganisms, and so on. The classification module 306 can be further configured to reclassify the individual colonies of the microorganisms/unknown microorganisms into the at least one species based on the inputs received from the user. In an example, the classification module 306 modifies the multi-categorical classification based on the inputs received from the user, and trains the mask RCNN with the modified multi-categorical classification. Thereafter, the classification module 306 feeds the media with the individual colonies again to the trained mask RCNN with the modified multi-categorical classification, that re-classifies the individual colonies/unknown microorganisms into the at least one type/species of microorganisms. The classification module 306 provides the media including the classified individual colonies to the counting module 308.

The counting module 308 can be configured to count the individual colonies of the at least one species by adding the number of each species of the colonies. The counting module 308 further generates the statistics report that indicating a number of colonies counted for each species of the microorganisms. The counting module 308 further stores the statistics report in the storage 108/memory 206. The counting module 308 also communicates the statistics report along with the received input media, and the output pixel overlays generated for the received input media to the user devices.

FIGS. 2 and 3 show exemplary blocks of the colony-counting device 106, but it is to be understood that other embodiments are not limited thereon. In other embodiments, the colony-counting device 106 may include less or more number of blocks. Further, the labels or names of the blocks are used only for illustrative purpose and does not limit the scope of the embodiments herein. One or more blocks can be combined together to perform same or substantially similar function in the colony-counting device 106.

Figure 4:
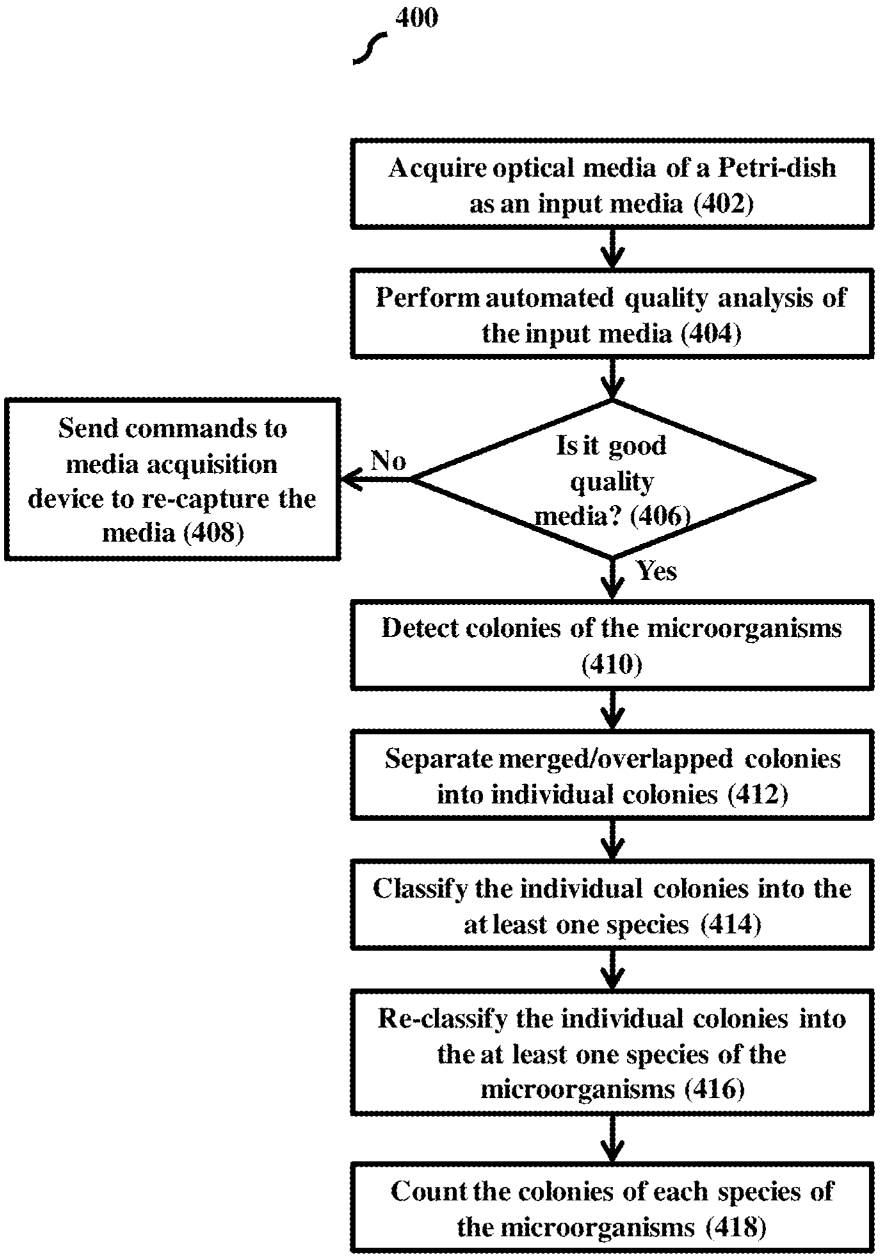
FIG. 4 is an example flow diagram depicting automated counting of the colonies of the microorganisms in the growth medium, according to embodiments as disclosed herein.

FIG. 4 is an example flow diagram 400 depicting automated counting of the colonies of the microorganisms in the growth medium, according to embodiments as disclosed herein. At step 402, the colony-counting device 106 receives the at least one optical media of the incubated dish as the input media from the at least one media acquisition device 104. The dish may or may not include the colonies of the microorganisms in the growth medium. At step 404, the colony-counting device 106 performs the automated quality analysis of the received input media. In an embodiment, the colony-counting device 106 compares the received input media with the reference high quality media and generates the SSIM. The colony-counting device 106 uses the generated SSIM to classify the input media into at least one of the good quality media, and the low quality media. In an embodiment, the colony-counting device 106 generates the compressed encoded data representation by encoding the data of the input media and reconstructs the output media using the encoded data representation. The colony-counting device 106 detects the differences between the input media and the associated reconstructed output media and according classifies the input media into the at least one quality type.

At step 406, the colony-counting device 106 checks the quality of the input media. At step 408, the colony-counting device 106 sends the commands to the at least one media acquisition device 104 to re-capture the media of the corresponding incubated dish on checking that the input media is the low quality media. At step 410, the colony-counting device 106 detects the colonies of the microorganisms in the growth medium disposed on the dish on checking that the input media is the good quality media. The colony-counting device 106 separates the foreground regions (including the colonies) from the background regions (including the dish) of the media. The colony-counting device 106 further detects the features of the foreground regions of the input media and compares the detected features with the labelled training data (including the original media of the specific colonies of the microorganisms and the associated features) to detect the colonies in the input media.

At step 412, the colony-counting device 106 separates/segregates the detected merged/overlapped colonies into the individual colonies of the microorganisms. The colony-counting device 106 generates the distance transform for the media with the detected merged colonies. The distance transform can be the gray scale/level image generated by changing the gray level intensities of points inside the foreground regions of the media including the detected colonies and illustrating the distance to the closest boundary from each point. The colony-counting device 106 further applies the watershed segmentation method on the distance transform to segregate the merged colonies into the individual colonies of the microorganisms.

At step 414, the colony-counting device 106 classifies the individual colonies of the microorganisms into at least one species of the microorganisms (can be the bacteria, the fungus, and any other unknown microorganisms). The colony-counting device 106 scans the feature maps of the media with the individual colonies and predicts the regions in the media with the colonies/objects. The colony-computing device 106 further assigns the predicted regions to the specific areas of the feature pyramid maps and compares the assigned specific areas of the feature pyramid maps with the multi-categorical classification to classify the colonies into the at least one species of microorganisms and to generate the output pixel overlays/mask.

At step 416, the colony-counting device 106 re-classifies the classified individual colonies/detected unknown microorganisms into at least one of the bacteria, the fungus, or the like. The colony-counting device 106 may also communicate the output pixels overlays of the media indicating the classification of the individual colonies into the at least one species to the user. The colony-counting device 106 receives the inputs from the user related to the classification of the individual colonies. Based on the received inputs, the colony-counting device 106 re-classifies the classified individual colonies/detected unknown microorganisms into the at least one species. At step 418, the colony-counting device 106 counts the number of the colonies of each species grown in the growth medium disposed on the dish. The various actions in method 400 may be performed in the order presented, in a different order or simultaneously. Further, in some embodiments, some actions listed in FIG. 4 may be omitted.

Figure 5:
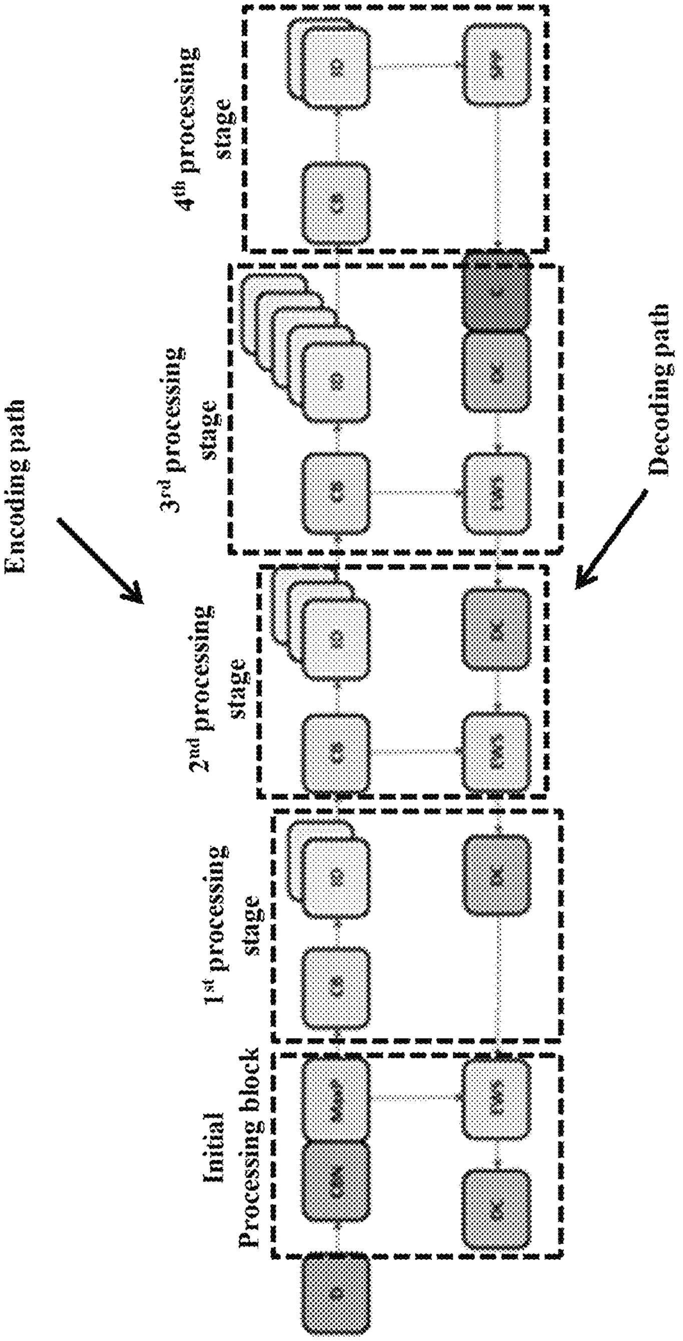
FIG. 5 depicts an example convolutional neural network (CNN) model used for detecting the colonies of the microorganisms in the growth medium, according to the embodiments as disclosed herein.

FIG. 5 depicts an example CNN model used for detecting the colonies of the microorganisms in the growth medium, according to the embodiments as disclosed herein. Embodiments herein are further explained considering the CNN with a residual network (ResNet) as an example for detecting the colonies of the microorganisms in the growth medium, but it may be obvious to a person skilled in the art that any other processing methods may be used. The CNN with the ResNet may include the at least one encoding path and the at least one decoding path, wherein the encoding path may be paired with the decoding path. In an example herein, the CNN with the ResNet may include four encoding paths and four decoding paths as depicted in FIG. 5. The encoding paths may include the initial processing block and a plurality of processing stages/layers. The initial processing block includes the CBN layer and the max pooling layer. Each processing stage includes the convolution block and the identity block. The convolution block and the identity block may include a plurality of convolutional layers. The decoding paths may include the SPP, the convolution layer (C), the EWS block, and the deconvolution layer (DC).

The colony-counting device 106 feeds the received input media to the encoding path of the CNN with the ResNet for detecting the colonies if the input media is of good quality. The initial processing block of the encoding path may separate the foreground regions from the background regions of the input media, and provides the foreground regions of the media to the plurality of processing stages of the encoding path. Each processing stage may extract the features of the foreground regions such as, but not limited to, color, texture, edges, corners, and so on and provide the extracted features to the next processing stages using the skip connection. The extracted features at each processing stage may be provided to the decoding path, which detects the colonies in the encoding path based on the labelled training data.

Figure 6A:
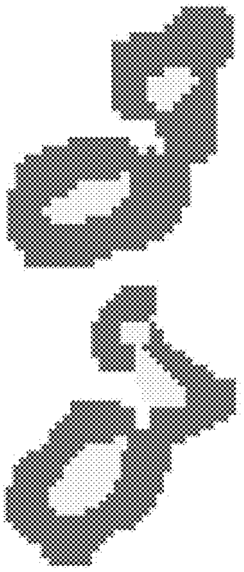
FIGS. 6*a*-6*b* depict separation of the merged colonies of the microorganisms into the individual colonies of the microorganisms, according to embodiments as disclosed herein.
Figure 6B:

FIGS. 6*a*-6*b* depict separation of the merged colonies of the microorganisms into the individual colonies of the microorganisms, according to embodiments as disclosed herein. Embodiments herein enable the colony-counting device 106 to count the colonies of the microorganisms by detecting the individual colonies of the microorganisms and classifying the individual colonies into the at least one species of the microorganism.

The colony-counting device 106 receives the at least one input media of the incubated dish from the at least one media acquisition device 104. The colony-counting device 106 detects the colonies of the microorganisms by evaluating the received input media/media if the received input media is the good quality media. In an example herein, consider that detected colonies can be the merged colonies of the microorganisms as depicted in FIG. 6*a*. In such a scenario, the colony-counting device 106 segregates the merged colonies into the individual colonies of the microorganisms using the distance transform and the watershed segmentation method as depicted in FIG. 6*b*. Thereafter, the colony-counting device 106 classifies the individual colonies into the at least one species of the microorganisms and counts the colonies of each species.

Figure 7:
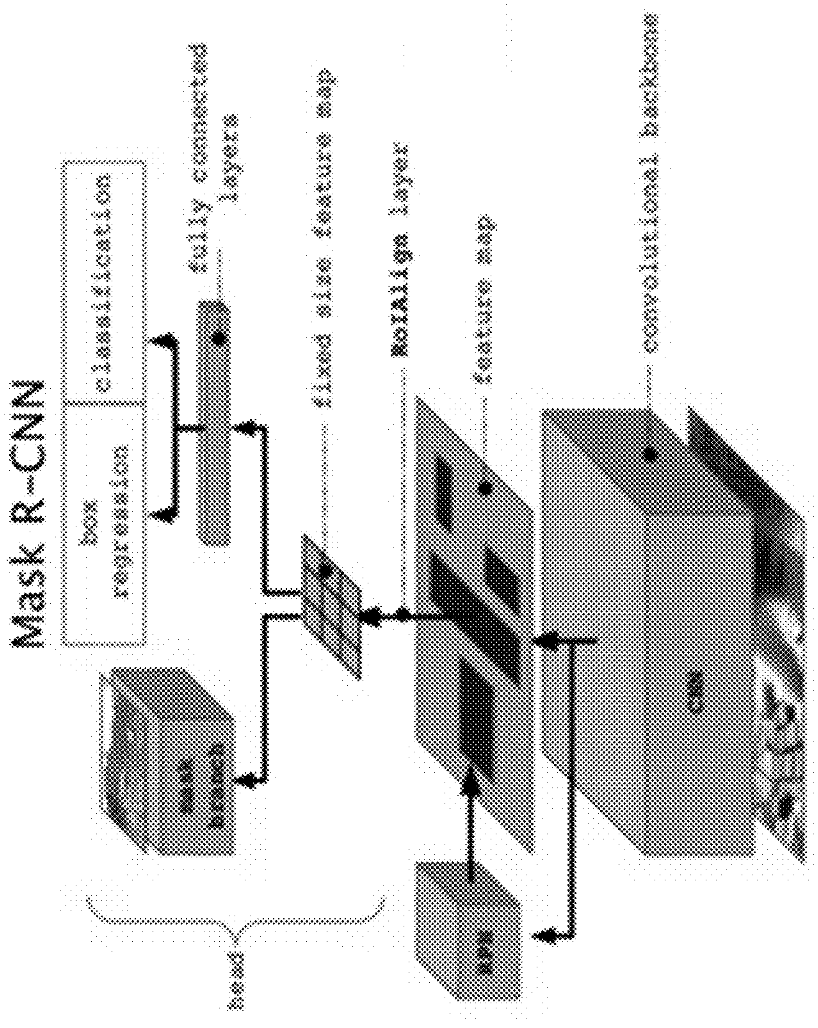
FIG. 7 depicts an example mask residual CNN (R-CNN) model for classifying the individual colonies into the at least one species of the microorganisms, according to embodiments as disclosed herein.

FIG. 7 depicts an example mask R-CNN model for classifying the individual colonies into the at least one species of the microorganisms, according to embodiments as disclosed herein.

Embodiments herein are further explained considering the mask RCNN as an example for classifying the microorganisms into the at least one type, but it may be obvious to a person skilled in the art that any other processing methods may be used. The mask RCNN may consist of the bottom-up pathway (for example: a ConvNet, a ResNet, and so on), the top-bottom pathway, and the lateral connections, wherein the bottom-up pathway and the top-bottom pathway may be connected to the lateral connections. The bottom-up pathway, the top-bottom pathway, and the lateral connections may include at least one of a CNN backbone, a Region Proposal Network (RPN), pooling layers, a mask branch, and fully connected layers.

The colony-counting device 106 may feed the media with the individual colonies into the bottom-up pathway of the mask RCNN. The bottom-up pathway scans the feature maps of the received media and proposes/predicts the regions with the objects/colonies. The top-bottom pathway generates the feature pyramid map, which can be similar to the feature map scanned by the bottom-up pathway. The top-bottom pathway assigns the predicted regions to specific areas of the feature pyramid maps, and maps the assigned specific areas of the feature pyramid maps with the multi-categorical classification to classify the detected individual colonies into the at least one species/type/class of microorganisms, generate the bounding boxes/free form contours and mask for the detected colonies.

Figure 8A:
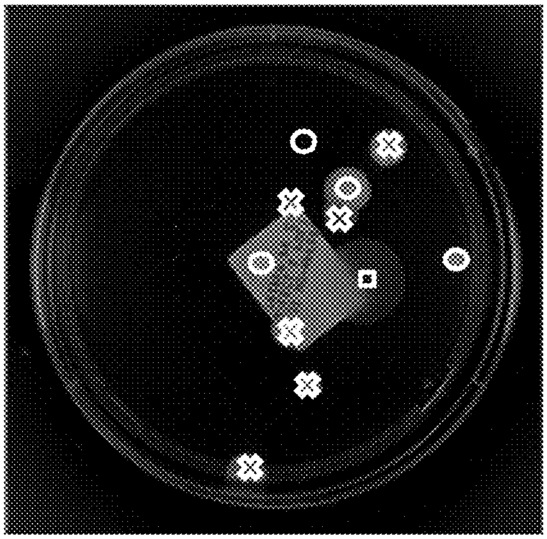
FIGS. 8*a* and 8*b* depict an input image of the incubated dish and an output image indicating the classification of the individual colonies of the microorganisms into the at least one species respectively, according to embodiments as disclosed herein.
Figure 8B:
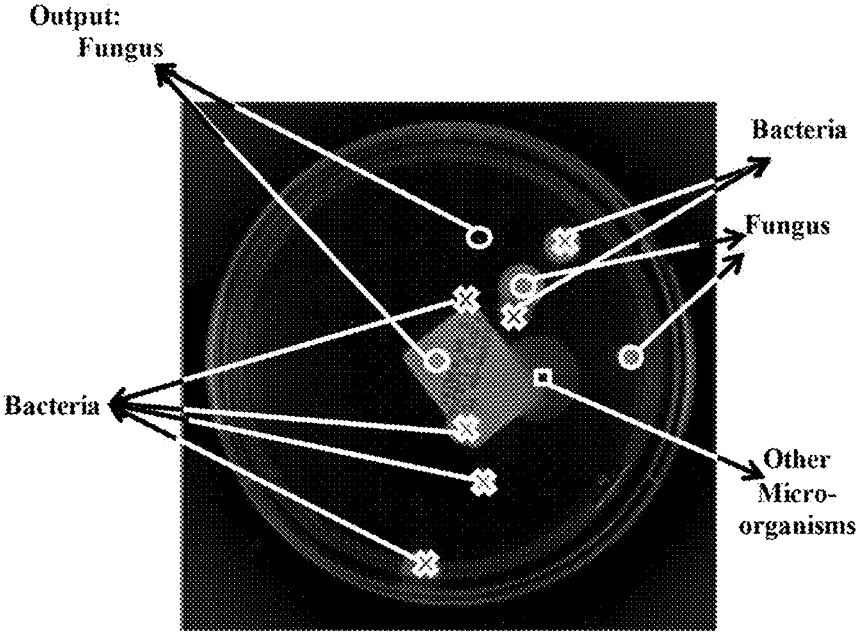

FIGS. 8*a* and 8*b* depict the input image of the incubated dish and the output image indicating the classification of the individual colonies of the microorganisms into the at least one species respectively, according to embodiments as disclosed herein. Consider an example scenario, wherein the colony-counting device 106 receives the at least one optical image of the incubated dish in the growth medium as the input image (as depicted in FIG. 8*a*) from the at least one media acquisition device 104. In such a scenario, the colony-counting device 106 analyzes the quality of the input image. If the input image is the good quality image, the colony-counting device 106 generates the output pixel overlays for the received input image as depicted in FIG. 8*b*. The output pixel overlays can be generated by detecting the individual colonies and/or merged/overlapped colonies, segregating the merged/overlapped colonies into the individual colonies of the microorganisms, and classifying the individual colonies into the at least one species of the microorganisms. In an example herein, the individual colonies are classified into the bacteria, the fungus, and the other unknown microorganisms as depicted in FIG. 8*b*. Further, the colony-counting device 106 may classify the other unknown microorganism into at least one of the bacteria, the fungus, or the like. In an embodiment herein, after classification, the colony-counting device 106 may denote each type of microorganism using at least one of, but not limited to, a symbol, a colour, a number, and so on. After classification, the colony-counting device 106 counts the colonies of each species that have been grown on the dish. In an example herein, consider that six colonies of the bacteria have been grown on the dish as depicted in FIG. 8*b*.

Figure 9:
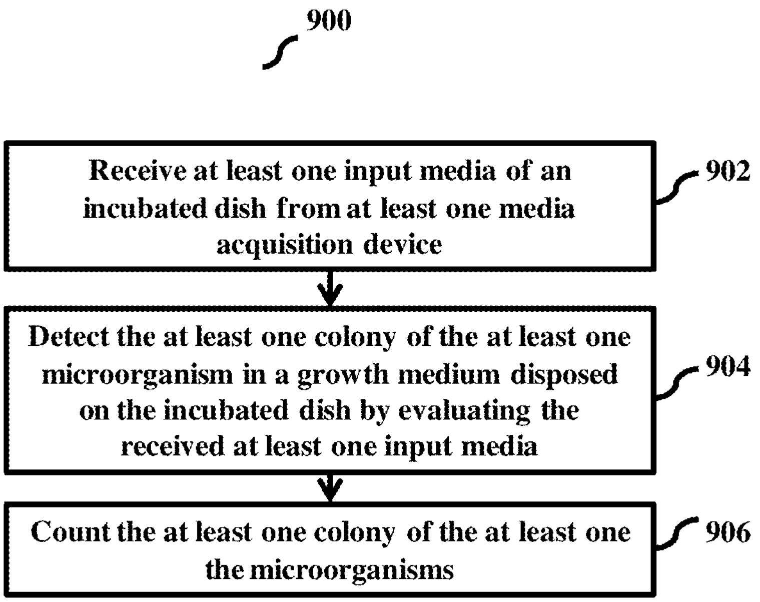
FIG. 9 is a flow chart depicting a method for counting the colonies of the microorganisms, according to the embodiments as disclosed herein.

FIG. 9 is a flow diagram 900 depicting a method for counting the colonies of the microorganisms, according to the embodiments as disclosed herein. At step 902, the method includes receiving, by the colony-counting device 106, the at least one input media of the dish/dish used for the growth of the at least one colony of the at least one microorganism from the at least one media acquisition device 104.

At step 904, the method includes detecting, by the colony-counting device 106, the at least one colony of the at least one microorganism in the growth medium disposed on the dish by evaluating the received at least one input media. The detection of the at least one colony includes analyzing the quality of the received at least one media and detecting the at least one colony if the received at least one media is the good quality media. The detected at least one colony can be at least one of the at least one individual colony, and the at least one grouped/merged colony.

At step 906, the method includes counting, by the colony-counting device 106, the at least one colony of each species of the microorganisms. The colony-counting device 106 counts the colonies of the microorganisms involves segregating the at least one grouped colony into the at least one individual colony, and classifying the at least one individual colony into the at least one species/type of the microorganisms. The various actions in method 900 may be performed in the order presented, in a different order or simultaneously. Further, in some embodiments, some actions listed in FIG. 9 may be omitted.

Embodiments herein automate/digitize a process of counting of colonies of microorganisms in a growth medium that is disposed on a dish.

Embodiments herein detect the colonies of the microorganisms and classify the colonies of the microorganisms into the at least one species using at least one learning method (for example, a deep neural network (DNN) model, an Artificial Intelligence (AI) model, a Machine Learning (ML) mode, and so on) for counting the colonies. Such a process of counting the colonies of the microorganisms results in reduced turnaround time and errors;

securing information about the counted colonies from unauthorized access; and in-enables quality management due to the digitization.

Embodiments herein count the colonies of the microorganisms in the absence of a well-trained technician, thus the counting of the colonies of the microorganisms can be consistent, accurate, and faster, which further increase yield in microbiology workflow.

The embodiments disclosed herein can be implemented through at least one software program running on at least one hardware device and performing network management functions to control the elements. The elements shown in FIGS. 1*a*-3 can be at least one of a hardware device, or a combination of hardware device and software module.

The embodiments disclosed herein describe methods and systems for automated counting and classifying of microorganisms. Therefore, it is understood that the scope of the protection is extended to such a program and in addition to a computer readable means having a message therein, such computer readable storage means contain program code means for implementation of one or more steps of the method, when the program runs on a server or mobile device or any suitable programmable device. The method is implemented in a preferred embodiment through or together with a software program written in e.g. Very high speed integrated circuit Hardware Description Language (VHDL) another programming language, or implemented by one or more VHDL or several software modules being executed on at least one hardware device. The hardware device can be any kind of portable device that can be programmed. The device may also include means which could be e.g. hardware means like e.g. an ASIC, or a combination of hardware and software means, e.g. an ASIC and an FPGA, or at least one microprocessor and at least one memory with software modules located therein. The method embodiments described herein could be implemented partly in hardware and partly in software. Alternatively, the invention may be implemented on different hardware devices, e.g. using a plurality of CPUs.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modification within the spirit and scope of the embodiments as described herein.

We claim:

1. A method for counting colonies of at least one microorganism, the method performed by a colony-counting device comprising a processor, the method comprising:

receiving at least one input media of an incubated dish from at least one media acquisition device;

performing automated quality analysis of the received at least one input media using at least one of reference-based methods and non-reference-based methods, wherein a quality type of the received at least one input media is classified as one of a good quality media or a low quality media;

if the received at least one input media is classified as the good quality media, detecting, by the colony-counting device through a colony detection and separation module using one or more neural network processing methods, at least one colony of the at least one microorganism in a growth medium disposed on the incubated dish by:

separating foreground regions including the at least one colony from background regions of the at least one input media, wherein the background regions include the incubated dish;

extracting features from the foreground regions to form a features map, wherein the features include at least one of color, texture, edges, and corners;

detecting the at least one colony of the at least one microorganism in the growth medium, if the extracted features map with labelled training data, wherein the labelled training data includes a plurality of original media including at least one specific colony of the at least one microorganism and associated label feature data;

counting, by a counting module using at least one learning method, wherein counting the colonies of the microorganisms comprises:

segregating, using a distance transform and a watershed segmentation method, at least one grouped colony into a first individual colony and a second individual colony;

classifying each of the first individual colony and the second individual colony into at least one species of the at least one microorganism;

generating at least one output pixel overlay including information about at least one of the at least one bounding box and the at least one free form contour of the at least one colony;

providing the at least one output pixel overlay to at least one user for validating the classification of the at least one colony of the at least one microorganism into the at least one species; and re-classifying the classified first and the second individual colonies into the at least one species of the at least one microorganism based on inputs received from the at least one user.

2. The method of claim 1, wherein detecting the at least one colony of the at least one microorganism comprises:

classifying the at least one input media as one of the good quality or the low quality, wherein the detected at least one colony includes at least one individual colony of the at least one microorganism and at least one grouped colony of the at least one microorganism;

segregating the at least one input media into a media with at least one colony;

detecting an absence of the at least one colony of the at least one microorganism in the growth medium, if the extracted features do not map with the labelled training data; and segregating the at least one input media into a media with zero colonies.

3. The method of claim 2, wherein analyzing the received at least one input media into the at least one quality type using the reference-based methods includes:

fetching at least one reference media from at least one of a storage and an external device, wherein the at least one reference media does not include the at least one colony of the at least one microorganism;

mapping the at least one reference media with the received at least one input media to generate a structural similarity index measurement (SSIM);

classifying the at least one input media into the good quality media, if the generated SSIM satisfies a pre-defined SSIM threshold; and classifying the at least one input media into the low quality media, if the generated SSIM does not satisfy the pre-defined SSIM threshold.

4. The method of claim 2, wherein analyzing the received at least one input media into the at least one quality type using the non-reference-based methods includes:

generating a compressed encoded data representation by encoding data of the at least one input media and compressing the encoded data;

reconstructing at least one output media using the encoded data representation;

detecting differences between the at least one input media and the reconstructed output media;

classifying the at least one input media into the good quality media, if the detected differences satisfy a pre-defined difference threshold; and classifying the at least one input media into the low quality media, if the detected differences do not satisfy the pre-defined difference threshold.

5. The method of claim 1, wherein counting the at least one colony of the at least one microorganism comprises:

checking whether the detected at least one colony includes at least one of:

the first individual colony, the second individual colony, and the at least one grouped colony;

if the detected at least one colony includes the at least one grouped colony, segregating the at least one grouped colony into the first individual colony and the second individual colony;

classifying each of the first individual colony and the second individual colony into at least one species of the at least one microorganisms, wherein classifying comprises:

predicting at least one region with the at least one colony by scanning at least one feature map of the foreground regions of the at least one media with the first individual colony and the second individual colony;

generating at least one feature pyramid map and assigning the predicted region with at least one specific area of the generated at least one feature pyramid map; and mapping the at least one specific area of the generated at least one feature pyramid map with a multi-categorical classification to classify the first and second individual colonies into the at least one species of the at least one microorganism;

generating at least one of:

at least one bounding box, at least one free form contour, wherein the at least one bounding box and the at least one free form contour indicate at least one boundary of the at least one colony, and at least one mask, wherein the at least one mask is associated at least one label indicating the at least one species of the at least one colony; and counting the at least one colony of each of the at least one species of the at least one microorganism.

6. The method of claim 5, wherein segregating the at least one grouped colony of the at least one microorganism includes:

computing the distance transform for the at least one grouped colony, comprising:

converting the foreground regions of the input media detected that include the at least one grouped colony into binary media; and generating a gray scale media by changing gray scale intensities of points inside the foreground regions and illustrating a distance from each pixel of each point to a non-zero valued pixel; wherein the non-zero valued pixel indicates a closest boundary from each point; and wherein the gray scale media is the distance transform; and segregating the at least one grouped colony into the first and the second individual colonies using the distance transform and the watershed segmentation method, comprising:

detecting the points of high scale intensities and low scale intensities in the distance transform, wherein the points of the high scale intensities denote peaks and the points of the low scale intensities denote valleys;

filling at least one isolated valley with at least one colored water; and building at least one barrier in at least one location wherein the at least one isolated valley with at least one different colored water merges recursively until the peaks are underwater, and wherein the built at least one barrier represents the segregation of the at least one grouped colony into the first and the second individual colonies of the at least one microorganism.

7. A colony-counting system comprising:

a colony-counting device, wherein the colony-counting device comprises:

a processor;

a non-transitory storage medium storing instructions;

a memory; and at least one media acquisition device;

wherein the processor is operably coupled to the memory and the at least one media acquisition device; and wherein the processor is configured to execute the instructions stored in the non-transitory storage medium to:

receive at least one input media of an incubated dish from the at least one media acquisition device;

perform automated quality analysis of the received at least one input media using at least one of reference-based methods and non-reference-based methods, wherein a quality type of the received at least one input media is classified as one of a good quality media or a low quality media;

if the received at least one input media is classified as good quality media, detect, through a colony detection and separation module using one or more neural network processing methods, at least one colony of the at least one microorganism in a growth medium disposed on the incubated dish by:

separating foreground regions including the at least one colony from background regions of the at least one input media, wherein the background regions include the incubated dish;

extracting features from the foreground regions to form a features map, wherein the features include at least one of color, texture, edges, and corners;

detecting the at least one colony of the at least one microorganism in the growth medium, if the extracted features map with labelled training data, wherein the labelled training data includes a plurality of original media including at least one specific colony of the at least one microorganism and associated label feature data;

count, through a counting module using at least one learning method, wherein the processor is configured to:

segregate, using a distance transform and a watershed segmentation method, at least one grouped colony into a first individual colony and a second individual colony;

classify each of the first and the second individual colonies into at least one species of the at least one microorganism;

generate at least one output pixel overlay including information about at least one of the at least one bounding box and the at least one free form contour of the at least one colony;

provide the at least one output pixel overlay to at least one user for validating the classification of the at least one colony of the at least one microorganism into the at least one species; and re-classify the classified first and the second individual colonies into the at least one species of the at least one microorganism based on inputs received from the at least one user.

8. The colony-counting system of claim 7, wherein the non-transitory storage medium further stores instructions that, when executed by the processor, cause the processor to:

detect the at least one colony of the at least one microorganism by analyzing the quality of the received at least one input media, wherein the labelled training data includes a plurality of original media including at least one specific colony of the at least one microorganism and associated label feature data, wherein the detected at least one colony includes at least one individual colony of the at least one microorganism and at least one grouped colony of the at least one microorganism;

segregate the at least one input media into a media with at least one colony;

if the extracted features do not map with the labelled training data:

detect an absence of the at least one colony of the at least one microorganism in the growth medium; and segregate the at least one input media into a media with zero colonies.

9. The colony-counting system of claim 8, wherein the non-transitory storage medium further stores instructions that, when executed by the processor, cause the processor to:

fetch at least one reference media from at least one of a storage or an external device, wherein the at least one reference media does not include the at least one colony of the at least one microorganism;

map the at least one reference media with the received at least one input media to generate a structural similarity index measurement (SSIM);

classify the at least one input media as good quality media, if the generated SSIM satisfies a pre-defined SSIM threshold; and classify the at least one input media as low quality media, if the generated SSIM does not satisfy the pre-defined SSIM threshold.

10. The colony-counting system of claim 8, wherein the non-transitory storage medium further stores instructions that, when executed by the processor, cause the processor to:

generate a compressed encoded data representation by encoding data of the at least one input media and compressing the encoded data;

reconstruct at least one output media using the encoded data representation;

detect differences between the at least one input media and the reconstructed output media;

classify the at least one input media as good quality media, if the detected differences satisfy a pre-defined difference threshold; and classify the at least one input media as low quality media, if the detected differences do not satisfy the pre-defined difference threshold.

11. The colony-counting system of claim 7, wherein the non-transitory storage medium further stores instructions that, when executed by the processor, cause the processor to:

check whether the detected at least one colony includes at least one of:

the first and the second individual colonies and the at least one grouped colony;

if the detected at least one colony includes the at least one grouped colony, segregate the at least one grouped colony into the first and the second individual colonies;

classify each of the first and the second individual colonies into at least one species of the of the at least one microorganism, wherein, for classifying, the non-transitory storage medium further stores instructions that, when executed by the processor, cause the processor:

predict at least one region with the at least one colony by scanning at least one feature map of the foreground regions of the at least one media with the first and the second individual colonies;

generate at least one feature pyramid map and assigning the predicted region with at least one specific area of the generated at least one feature pyramid map; and map the at least one specific area of the generated at least one feature pyramid map with a multi-categorical classification to classify the first and second individual colonies into the at least one species of the at least one microorganism;

generate at least one of:

at least one bounding box, at least one free form contour wherein the at least one bounding box and the at least one free form contour indicate at least one boundary of the at least one colony, and at least one mask, and wherein the at least one mask is associated at least one label indicating the at least one species of the at least one colony; and count the at least one colony of each of the at least one species of the at least one microorganism.

12. The colony-counting system of claim 11, wherein the non-transitory storage medium further stores instructions that, when executed by the processor, cause the processor to:

compute a distance transform for the at least one grouped colony, wherein, for computing the distance transform, the non-transitory storage medium further stores instructions that, when executed by the processor, cause the processor to:

convert the foreground regions of the input media that include the at least one grouped colony into binary media; and generate a gray scale media by changing gray scale intensities of points inside the foreground regions and illustrating a distance from each pixel of each point to a non-zero valued pixel; wherein the non-zero valued pixel indicates a closest boundary from each point; and wherein the gray scale media is the distance transform; and segregate the at least one grouped colony into the first and the second individual colonies using the distance transform and the watershed segmentation method, wherein, for segregating the at least one grouped colony, the non-transitory storage medium further stores instructions that, when executed by the processor, cause the processor to:

detect the points of high scale intensities and low scale intensities in the distance transform, wherein the points of the high scale intensities denote peaks and the points of the low scale intensities denote valleys;

fill at least one isolated valley with at least one colored water; and build at least one barrier in at least one location wherein the at least one isolated valley with the at least one colored water merge recursively until the peaks are underwater, and wherein the built at least one barrier represents the segregation of the at least one grouped colony into the first and the second individual colonies of the at least one microorganism.

* * * * *